United States Patent [19]

Stetter et al.

[11] Patent Number: 4,774,254

[45] Date of Patent: Sep. 27, 1988

[54] METHOD OF COMBATTING INSECTS AND ACARIDS USING 1-ARYL-4-TRIFLUOROMETHYL-5-AMINOPYRAZOLE

[75] Inventors: Jörg Stetter, Wuppertal; Otto Schallner, Monheim; Markus Lindig, Hilden; Uta Jensen-Korte, Düsseldorf; Bernd Baasner, Leverkusen; Benedikt Becker, Mettmann; Bernhard Homeyer, Leverkusen; Wolfgang Behrenz, Overath; Wilhelm Stendel, Wuppertal, all of Fed. Rep. of Germany

[73] Assignee: Bayer Aktiengesellschaft, Leverkusen, Fed. Rep. of Germany

[21] Appl. No.: 27,709

[22] Filed: Mar. 19, 1987

[30] Foreign Application Priority Data

Mar. 20, 1986 [DE] Fed. Rep. of Germany ....... 3609423

[51] Int. Cl.⁴ ............................................. A02H 43/56
[52] U.S. Cl. ..................................... 514/404; 514/341; 514/407; 546/279; 548/362; 548/377
[58] Field of Search ............... 548/362, 377; 514/407, 514/341, 404; 546/279

[56] References Cited

U.S. PATENT DOCUMENTS 4,127,575 11/1978 McGregor ......................... 546/345
4,614,533 9/1986 Schallner et al. ....................... 71/92

FOREIGN PATENT DOCUMENTS 0154115 9/1985 European Pat. Off. ................. 71/92
2819932 11/1979 Fed. Rep. of Germany ...... 548/375
2839270 3/1980 Fed. Rep. of Germany ...... 548/375
2912494 10/1980 Fed. Rep. of Germany ...... 548/375

OTHER PUBLICATIONS

Pharmaco. Ed. Sci. 26, 276–293 (1971).
Mycopathologica 74, 7–14 (1981).
Chemical Abstract 96 196411j (1982).

Chemical Abstract 95, 36257 q (1981).
J. Org. Chem. 36, 2972–2974 (1971).
J. Heterocyclic Chemistry 7, 345–349 (1970).
Methods of Oganic Chemistry, vol. X, 2 p. 203 (1967), "Methoden der organischem Chemie".
F. Arndt et al, Ann. 521, 95 (1935).
J. Hori et al, Sci. Papers Inst. Phys. Chem. Res. p. 56 (1962).

*Primary Examiner*—Mary C. Lee
*Assistant Examiner*—Kurt G. Briscoe
*Attorney, Agent, or Firm*—Sprung Horn Kramer & Woods

[57] ABSTRACT

A method of combating insects and acarids which comprises applying to such insects, acarids or a habitat thereof, an insecticidally or acaricidally effective amount of a 5-amino-1-aryl-pyrazole of the formula

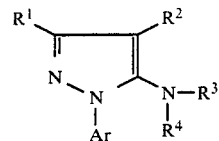

in which
$R^1$ represents hydrogen, alkyl or halogenoalkyl,
$R^2$ represents trifluoromethyl,
$R^3$ represents hydrogen, alkyl or alkenyl,
$R^4$ represents hydrogen, alkyl, alkenyl, alkinyl or a

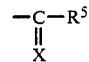

radical, and
Ar represents in each case optionally substituted phenyl or pyridyl, where X represents oxygen or sulphur, and $R^5$ denotes alkyl or halogenoalkyl.

Some of the compounds are new.

4 Claims, No Drawings

METHOD OF COMBATTING INSECTS AND ACARIDS USING 1-ARYL-4-TRIFLUOROMETHYL-5-AMINOPYRAZOLE

The invention relates to the use of 5-aminopyrazole derivatives, some of which are known as pesticides, particularly as insecticides and acaricides.

It has already been disclosed that N,N-dimethyl-O-pyrazol-carbamin-acid-esters exhibit an insecticidal efficacy. As to this compare with DE-OS (German Published Specification) No. 2,839,270.

However, the strength of action or the duration of action of these compounds is not always completely satisfactory, particularly for certain insects or at low applicational concentrations.

Finally, certain 5-amino-1-aryl-pyrazoles are known (cf., for example, Pharmaco, Ed. Sci. 26, 276–293 (1971) Mycopathologica 74, 7–14 (1981) or C.A. 96: 196411j and C.A. 95: 36257 q, U.S. Pat. No. 4,614,533.

However, nothing is known about the effectiveness of this class of compound against insects or mites.

It has been found that the 5-aminopyrazoles of the general formula (I)

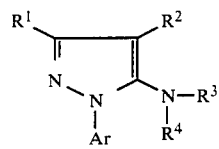 (I)

in which
R$^1$ represents hydrogen, alkyl or halogenoalkyl,
R$^2$ represents trifluoromethyl,
R$^3$ represents hydrogen, alkyl or alkenyl,
R$^4$ represents hydrogen, alkyl, alkenyl, alkinyl or a

radical,
Ar represents in each case optionally substituted phenyl or pyridyl,
where X represents oxygen or sulphur,
and R$^5$ denotes alkyl or halogenoalkyl, some of which are known, have strongly developed insecticidal and acaricidal properties.

Surprisingly, the 5-aminopyrazoles of the general formula (I), to be used according to the invention, display a considerably improved insecticidal, acaricidal and nematicidal effectiveness than the pyrazole derivatives known from the prior art.

The 5-aminopyrazole derivatives to be used according to the invention are generally defined by the formula (I). Preferred compounds of the formula (I) are those in which
R$^1$ represents in each case straight-chain or branched alkyl or halogenoalkyl having 1 to 4 carbon atoms and, if appropriate, 1 to 9 identical or different halogen atoms, or hydrogen,
R$^2$ represents trifluoromethyl,
R$^3$ represents hydrogen, C$_1$–C$_6$-alkyl or C$_2$–C$_6$-alkenyl,
R$^4$ represents hydrogen, C$_1$–C$_6$-alkyl, C$_2$–C$_6$-alkenyl, C$_2$–C$_6$-alkinyl or a

radical, where R$^5$ represents C$_1$–C$_4$-alkyl or C$_1$–C$_4$-halogenoalkyl,
Ar represents in each case optionally mono- or poly-substituted phenyl, 2-pyridyl, 3-pyridyl or 4-pyridyl, the substituents being identical or different and suitable substituents being: cyano, nitro, halogen, in each case straight-chain or branched alkyl, alkoxy or alkoxycarbonyl each having up to 4 carbon atoms, in addition in each case straight-chain or branched halogenoalkyl or halogenoalkoxy each having up to 4 carbon atoms and up to 9 identical or different halogen atoms, or an —S(O)$_m$—R$^6$ radical where
R$^6$ represents amino, and in each case straight-chain or branched alkyl, alkylamino, dialkylamino or halogenoalkyl each having up to 4 carbon atoms in the individual alkyl parts and, in the case of halogenoalkyl, having up to 9 identical or different halogen atoms, and
m represents a number 0, 1 or 2.

Particularly preferred compounds of the formula (I) are those in which
R$^1$ represents hydrogen, methyl, ethyl, n- or i-propyl or trifluoromethyl,
R$^2$ represents trifluoromethyl,
R$^3$ represents hydrogen, methyl, ethyl, n- or i-propyl, n-, i-, s- or t-butyl, n- or i-pentyl, n- or i-hexyl, vinyl, prop-1-enyl, prop-2-enyl, but-1-enyl or but-2-enyl,
R$^4$ represents hydrogen, methyl, ethyl, n- or i-propyl, n-, i-, s- or t-butyl, n- or i-pentyl, n- or i-hexyl, propargyl, but-1-inyl, but-2inyl or one of the following radicals:

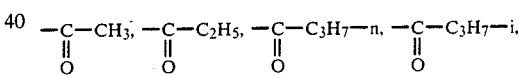

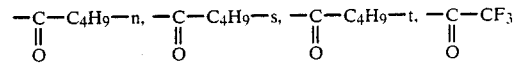

Ar represents in each case optionally mono- to pentasubstitued phenyl, 2-pyridyl, 3-pyridyl or 4-pyridyl, the substituents being identical or different and suitable substituents being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, difluorochloromethyl, dichlorofluoromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or an —S(O)$_m$—R$^6$ radical, where
R$^6$ represents amino, methylamino, ethylamino, dimethylamino, diethylamino, fluorodichloromethyl, difluoromethyl, tetrafluoroethyl, trifluorochloroethyl, trifluoromethyl, methyl or ethyl, and m represents a number 0, 1 or 2.

Apart from the compounds mentioned in the case of the preparation examples, the following 5-aminopyrazoles of the general formula (I) may be mentioned individually:

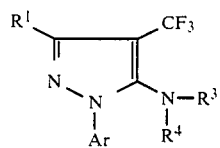

| $R^1$ | $R^3$ | $R^4$ | Ar |
|---|---|---|---|
| H | $CH_3$ | H | 2,4-Cl, 5-$CF_3$-phenyl |
| H | $C_2H_5$ | H | 2,4-Cl, 5-$CF_3$-phenyl |
| H | $-CH_2-CH=CH_2$ | H | 2,4-Cl, 5-$CF_3$-phenyl |
| $CH_3$ | H | H | 2,4-Cl, 5-$CF_3$-phenyl |
| $CH_3$ | $CH_3$ | H | 2,4-Cl, 5-$CF_3$-phenyl |
| $CF_3$ | H | H | 2,4-Cl, 5-$CF_3$-phenyl |
| $CF_3$ | $CH_3$ | H | 2,4-Cl, 5-$CF_3$-phenyl |

-continued

| $R^1$ | $R^3$ | $R^4$ | Ar |
|---|---|---|---|
| $CH_3$ | H | $COCH_3$ | 2,6-Cl, 4-$CF_3$-phenyl |
| H | H | H | 5-Cl-pyridin-2-yl |
| H | $CH_3$ | H | 5-Cl-pyridin-2-yl |
| H | $C_2H_5$ | H | 5-Cl-pyridin-2-yl |
| $CH_3$ | H | H | 5-Cl-pyridin-2-yl |
| $CH_3$ | $CH_3$ | H | 5-Cl-pyridin-2-yl |
| $CF_3$ | H | H | 5-Cl-pyridin-2-yl |
| $CF_3$ | $CH_3$ | H | 5-Cl-pyridin-2-yl |
| H | H | $COCH_3$ | 5-Cl-pyridin-2-yl |
| $CH_3$ | H | $COCH_3$ | 5-Cl-pyridin-2-yl |
| $C_2H_5$ | $CH_3$ | $COCH_3$ | 5-Cl-pyridin-2-yl |

-continued

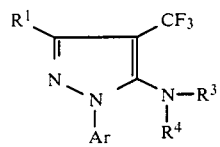

| R¹ | R³ | R⁴ | Ar |
|---|---|---|---|
| H | H | H | 2,6-difluoro-4-(CF₃)phenyl |
| H | CH₃ | H | 2,6-difluoro-4-(CF₃)phenyl |
| H | C₂H₅ | H | 2,6-difluoro-4-(CF₃)phenyl |
| H | —CH₂—CH=CH₂ | H | 2,6-difluoro-4-(CF₃)phenyl |
| CH₃ | H | H | 2,6-difluoro-4-(CF₃)phenyl |
| CH₃ | CH₃ | H | 2,6-difluoro-4-(CF₃)phenyl |
| CF₃ | H | H | 2,6-difluoro-4-(CF₃)phenyl |
| CF₃ | CH₃ | H | 2,6-difluoro-4-(CF₃)phenyl |

-continued

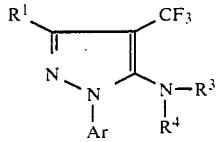

| R¹ | R³ | R⁴ | Ar |
|---|---|---|---|
| H | H | COCH₃ | 2,6-difluoro-4-(CF₃)phenyl |
| CH₃ | H | COCH₃ | 2,6-difluoro-4-(CF₃)phenyl |
| C₂H₅ | CH₃ | H | 2,6-difluoro-4-(CF₃)phenyl |
| H | H | H | 2,6-dichloro-4-(CF₃)phenyl (Br instead of one Cl) — 2-bromo-6-chloro-4-(CF₃)phenyl |
| H | CH₃ | H | 2-bromo-6-chloro-4-(CF₃)phenyl |
| H | C₂H₅ | H | 2-bromo-6-chloro-4-(CF₃)phenyl |
| H | —CH₂—CH=CH₂ | H | 2-bromo-6-chloro-4-(CF₃)phenyl |
| CH₃ | H | H | 2-bromo-6-chloro-4-(CF₃)phenyl |

-continued
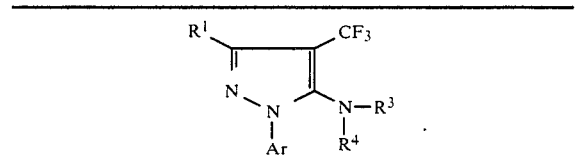
| R¹ | R³ | R⁴ | Ar |
|---|---|---|---|
| CH₃ | CH₃ | H | 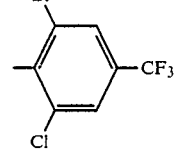 |
| CF₃ | H | H | 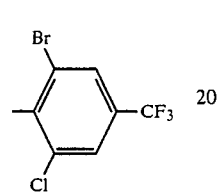 |
| CF₃ | CH₃ | H | 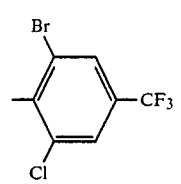 |
| H | H | COCH₃ | 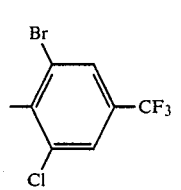 |
| CH₃ | H | COCH₃ | 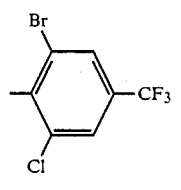 |
| C₂H₅ | CH₃ | H | 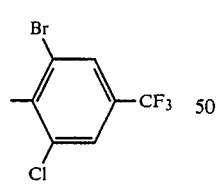 |
| H | H | H | 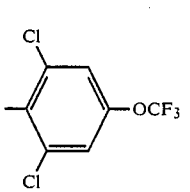 |
| H | CH₃ | H | 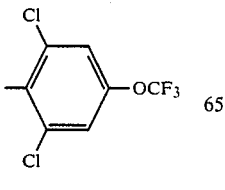 |
-continued
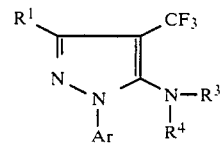
| R¹ | R³ | R⁴ | Ar |
|---|---|---|---|
| H | C₂H₅ | H | 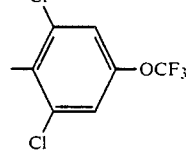 |
| H | —CH₂—CH=CH₂ | H | 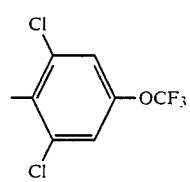 |
| CH₃ | H | H |  |
| CH₃ | CH₃ | H |  |
| CF₃ | H | H |  |
| CF₃ | CH₃ | H |  |
| H | H | COCH₃ | 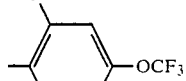 |
| CH₃ | H | COCH₃ |  |

-continued $$\begin{array}{c} R^1 \quad\quad CF_3 \\ \diagdown \quad \diagup \\ N \quad\quad N-R^3 \\ \diagdown N \diagup \quad | \\ | \quad\quad R^4 \\ Ar \end{array}$$

| R¹ | R³ | R⁴ | Ar |
|---|---|---|---|
| H | H | —CH₂—C≡CH | 3,5-dichloro-4-OCF₃-phenyl |
| C₂H₅ | CH₃ | H | 3,5-dichloro-4-OCF₃-phenyl |
| H | H | H | 2-Cl-4-CF₃-phenyl |
| H | CH₃ | H | 2-Cl-4-CF₃-phenyl |
| H | C₂H₅ | H | 2-Cl-4-CF₃-phenyl |
| H | —CH₂—CH=CH₂ | H | 2-Cl-4-CF₃-phenyl |
| CH₃ | H | H | 2-Cl-4-CF₃-phenyl |
| CH₃ | CH₃ | H | 2-Cl-4-CF₃-phenyl |
| CF₃ | H | H | 2-Cl-4-CF₃-phenyl |

-continued $$\begin{array}{c} R^1 \quad\quad CF_3 \\ \diagdown \quad \diagup \\ N \quad\quad N-R^3 \\ \diagdown N \diagup \quad | \\ | \quad\quad R^4 \\ Ar \end{array}$$

| R¹ | R³ | R⁴ | Ar |
|---|---|---|---|
| CF₃ | CH₃ | H | 2-Cl-4-CF₃-phenyl |
| H | H | COCH₃ | 2-Cl-4-CF₃-phenyl |
| CH₃ | H | COCH₃ | 2-Cl-4-CF₃-phenyl |
| C₂H₅ | H | H | 2-Cl-4-CF₃-phenyl |
| C₂H₅ | CH₃ | H | 2-Cl-4-CF₃-phenyl |
| H | CH₃ | CH₃ | 2-Cl-4-CF₃-phenyl |

Some of the 5-aminopyrazoles of the formula (I), to be used according to the invention, are known (cf. DE-OS (German Published Specification) No. 3,402,308) and can be obtained analogously to the preparation methods described there.

Substituted 5-amino-1-phenyl-pyrazoles of the formula (Ia)

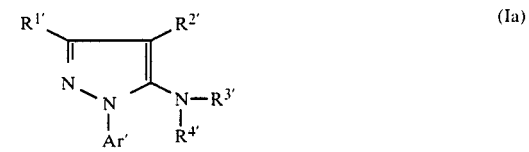

(Ia)

in which
R¹' represents hydrogen, alkyl or halogenoalkyl,
R²' represents trifluoromethyl,
R³' represents hydrogen, alkyl or alkenyl,
R⁴' represents hydrogen, alkyl, alkenyl, alkinyl or a

radical,

Ar' represents in each case optionally substituted phenyl or pyridyl, where

X represents oxygen or sulphur, and $R^{5'}$ represents alkyl or halogenoalkyl, where, if $R^{1'}$ represents hydrogen, the radicals $R^{3'}$, $R^{4'}$ and Ar' may not have the following combinations of meanings:

$R^{3'}$=hydrogen, $R^{4'}$=hydrogen and Ar'=2,4,6-trichlorophenyl or 2,4,6-trinitrophenyl;

$R^{3'}$=hydrogen, $R^{4'}$=COCH$_3$ and Ar'=2,6,dichloro-4-trifluoromethylphenyl or 2,6-dichloro-4-trifluoromethyloxyphenyl;

$R^{3'}$=hydrogen, $R^{4'}$=COC$_2$H$_5$ and Ar'=2,6-dichloro-4-trifluoromethylthiophenyl or 2,3,6-trifluoro-4-trifluoromethylthiophenyl;

$R^{3'}$=methyl, $R^{4'}$=COCH$_3$ and Ar'=2-chloro-4-trifluoromethyl, are not yet known.

(a) The 1-aryl-5-amino-4-trifluoromethylpyrazoles of the formula (Ia) are obtained when 1-aryl-5-amino-4-carboxypyrazoles of the formula (II)

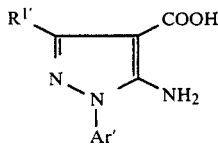

in which $R^{1'}$ and Ar' have the abovementioned meaning, are reacted with sulphur tetrafluoride in hydrofluoric acid under increased pressure, and the resulting compounds of the formula

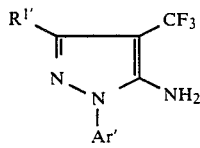

are, if appropriate, alkylated, alkenylated, alkinylated or acylated, or (b) the 1-aryl-5-amino-4-trifluoromethylpyrazoles of the formula

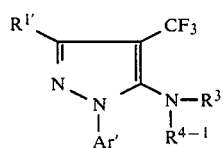

in which $R^{4-1}$ represents alkyl, alkenyl, alkinyl or a

radical, and $R^{1'}$, $R^{3'}$, $R^{5'}$, Ar' and X have the abovementioned meaning, are obtained when 1-aryl-5-amino-4-trifluoromethylpyrazoles of the formula

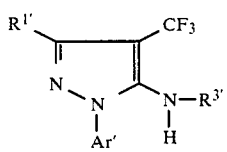

in which $R^{1'}$, $R^{3'}$ and Ar' have the abovementioned meaning, are reacted with compounds of the formula $$R^{4-1}-A \qquad (III)$$

in which $R^{4-1}$ represents alkyl, alkenyl, alkinyl or a

radical, where $R^{5'}$ and X have the abovementioned meaning, and

A represents an electron-withdrawing leaving group, if appropriate in the presence of a diluent and if appropriate in the presence of an acid acceptor, or (c) the 1-aryl-5-amino-4-trifluoromethylpyrazoles of the formula

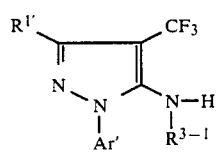

in which $R^{1'}$ and Ar' have the abovementioned meaning, and $R^{3-1}$ represents alkyl or alkenyl, are obtained by deacylating 5-(N-acylamino)-4-trifluoromethyl-1-arylpyrazoles of the formula

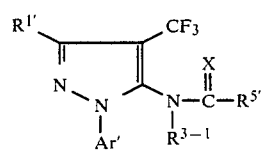

in which $R^{1'}$, $R^{5'}$, $R^{3-1}$, X and Ar' have the abovementioned meaning, with acids or bases, if appropriate in the presence of a diluent, or (d) the 1-aryl-5-amino-trifluoromethylpyrazoles of the formula

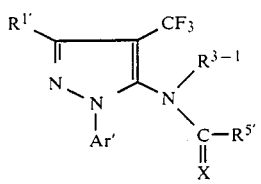

(Ig)

in which

R¹', R³⁻¹, R⁵', X and Ar' have the abovementioned meaning, are obtained by reacting 1-aryl-5-amino-trifluoromethylpyrazoles of the formula

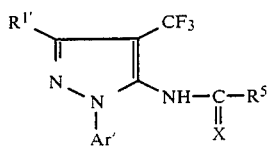

(Ih)

with compounds of the formula R³⁻¹—A in which

R³⁻¹ has the abovementioned meaning and A represents a leaving group.

If 1-(2,6-dichloro-4-trifluoromethylphenyl)-4-carboxy-5-aminopyrazole and sulphur tetrafluoride are used as starting materials in the preparation version (a), then the course of the reaction can be represented by the following equation:

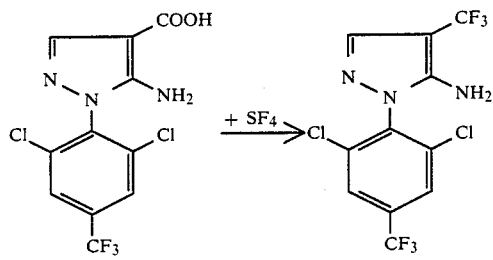

If 1-(2,6-dichloro-4-trifluoromethyl-phenyl)-3-methyl-4-trifluoromethyl-5-aminopyrazole and propionyl chloride are used as starting materials in the preparation version (b), then the course of the reaction can be represented by the following equation:

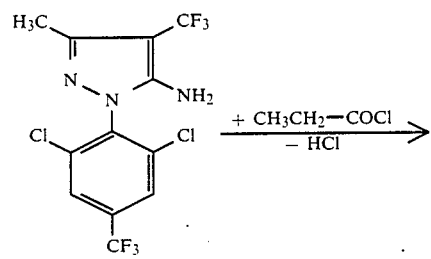

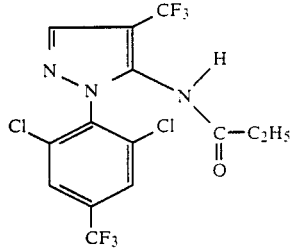

If 1-(2,6-dichloro-4-trifluoromethylphenyl)-4-trifluoromethyl-5-acetylamino-pyrazole and ethyl chloride are used as starting compounds in the preparation version (d), then the course of the reaction can be represented as follows:

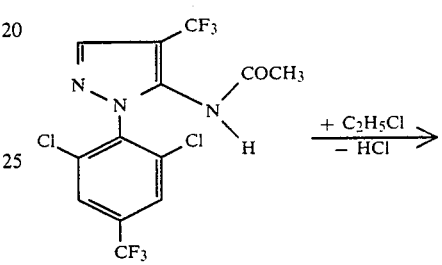

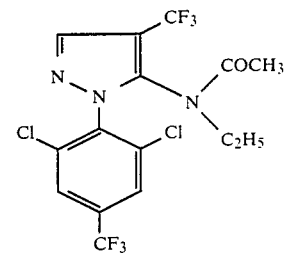

If 1-(2,6-dichloro-4-trifluoro-methylphenyl)-4-trifluoromethyl-5-(ethyl-acetylamino)-pyrazole is used as starting compound in the preparation version (c) and sodium hydroxide is used as base, then the course of the reaction can be represented as follows:

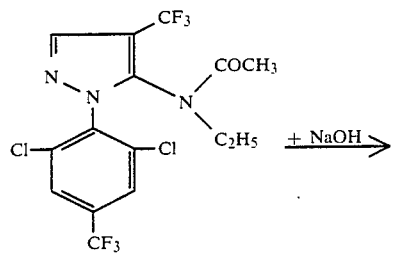

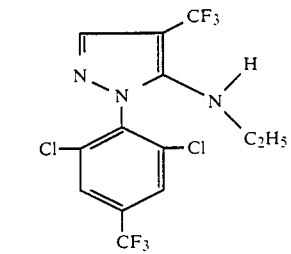

The 1-aryl-5-amino-4-carboxypyrazoles required as starting materials for carrying out the process (a) according to the invention are generally defined by the formula (II).

In this formula, $R^1$ and Ar preferably represent those radicals which have already been mentioned in connection with the description of the substances of the formula (I) as being preferred for these substituents.

Some of the 1-aryl-5-amino-4-carboxypyrazoles of the formula (II)

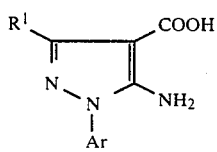     (II)

are known (cf., for example, J. Org. Chem. 36, 2972–2974 [1971] or J. Heterocyclic Chemistry 7, 345–349 [1970], C.A. 62: 13137 c).

They are obtained, for example, by reacting arylhydrazines of the formula

     (IV)

in which
Ar has the abovementioned meaning,
with acrylonitrile derivatives of the formula

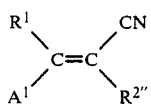     (V)

in which
$R^1$ represents hydrogen, alkyl or halogenoalkyl,
$R^{2''}$ represents alkoxycarbonyl, and
$A^1$ represents halogen, hydroxy, alkoxy, amino or dialkylamino,
either initially in a first stage, if appropriate in the presence of a diluent such as, for example, ethanol or glacial acetic acid, and if appropriate in the presence of a reaction auxiliary such as, for example, sodium acetate, at temperatures between $-20°$ C. and $+20°$ C. to form the arylhydrazine derivatives of the formula (VI),

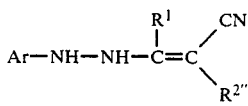     (VI)

in which
Ar, $R^1$ and $R^{2''}$ have the abovementioned meaning,
and cyclizing this in a second stage, if appropriate in the presence of a diluent such as, for example, ethylene glycol monoethyl ether, at temperatures between $+50°$ C. and $+150°$ C., or cyclizing directly in one reaction step, without isolation of the intermediate of the formula (VI), if appropriate in the presence of a diluent such as, for example, ethylene glycol monoethyl ether, at temperatures between $+50°$ C. and $+150°$ C., to form the 5-aminopyrazoles of the formula (VII)

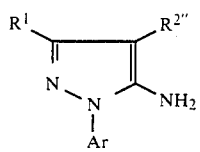     (VII)

in which
$R^1$, $R^{2''}$ and Ar have the abovementioned meaning,
and saponifying the 5-amino-pyrazole derivatives of the formula (VI) obtained in a generally conventional fashion, if appropriate in the presence of a diluent, such as, for example, ethanol or isopropanol, at temperatures between $+20°$ C. and $140°$ C., to form 4-carboxy-5-amino-pyrazoles of the formula (II)

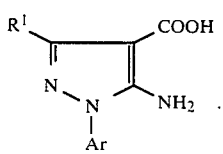     (II)

The arylhydrazines of the formula

     (IV)

are known (cf., for example, U.S. Pat. No. 4,127,575; U.S. Pat. No. 3,609,158; DE-OS (German Published Specification No. 2,558,399; J. Chem. Soc. C, 1971, 167–174) or they can be prepared in a simple analogous fashion by processes which are known in principle (cf., for example, Houben-Weyl, "Methoden der organischen Chemie" [Methods of Organic Chemistry], Volume X, 2 p. 203, Thieme Verlag Stuttgart 1967).

The acrylonitrile derivatives of the formula (V)

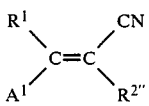     (V)

are generally known compounds of organic chemistry. The compounds of the structure (Va)

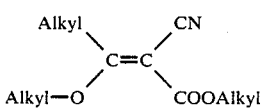     (Va)

where Alkyl represents an alkyl radical (preferably $C_1$–$C_6$-alkyl), are known, for example, from Beilstein E II 3, p. 301, F. Arndt et al., Ann. 521, 95 (1935), T. Hayashi et al., J.O.C. 30, 695 (1965), J. Hori et al., Sci. Papers Inst. Phys. Chem. Res. 56, 216 (1962).

The acrylonitrile derivatives of the formula (V)

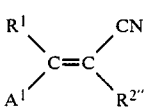     (V)

where
$R^1$ represents lower alkyl,
$A^1$ represents lower alkoxy, and $R^{2''}$ represents alkoxycarbonyl,
can be obtained, for example, by reaction of cyanoacetates with orthoesters, such as, for example, by the following reactions:

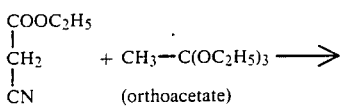

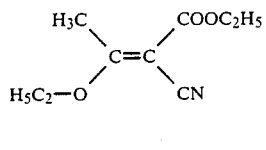

or

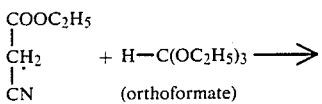

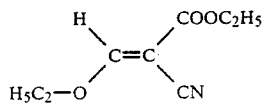

The 1-aryl-5-amino-4-trifluoromethylpyrazoles required as starting materials for carrying out the process version (b) are generally defined by the formula (Ic).

In this formula, $R^1$, $R^3$ and Ar preferably represent those radicals which have already been mentioned in connection with the description of the substances of the formula (I) as being preferred for these substituents.

The compounds of the formula (Ic) are compounds according to the invention, and are obtained, for example, using process version (a) or (d).

The compounds which are furthermore required as starting materials for carrying out the process (b) are generally defined by the formula (III). In this formula, A preferably represents chlorine, bromine, iodine, p-toluenesulphonyloxy, alkoxysulphonyloxy or acyloxy, $R^{4\text{-}1}$ preferably represents alkyl having 1 to 8 carbon atoms, alkenyl or alkinyl each having 2 to 8 carbon atoms, or the

radical where X preferably represents an oxygen atom and $R^5$ preferably represents alkyl having 1 to 8 carbon atoms.

The 5-(N-acylamino)-4-trifluoromethyl-1-arylpyrazoles required as starting materials for carrying out the process version (c) are generally defined by the formula (If).

In this formula, $R^{1'}$, $R^{5'}$, X and Ar' preferably represent those radicals which have already been specified in connection with the definition of compounds of the formula (I). $R^{3\text{-}1}$ preferably represents alkyl having 1 to 8 carbon atoms or alkenyl having 2 to 8 carbon atoms.

The compounds of the formula (If) are compounds according to the invention and can be obtained using process version (b) or (d).

In process version (a), compounds of the formula (II) are reacted with hydrofluoric acid and sulphur tetrafluoride, preferably in an autoclave, if appropriate under an inert gas atmosphere (particularly nitrogen atmosphere), i.e. under increased pressure for several hours at temperatures from 60°–200° C., particularly from 80°–150° C., the pressure is released, the hydrofluoric acid still remaining is removed by distillation, and the residue is worked up in a fashion which is known per se (for example by pouring onto ice water, dropwise addition of alkali metal hydroxide solution, washing with an organic solvent and chromatographic purification of the final product).

During this process, 10 to 100 mols of hydrofluoric acid and 1.5 to 10 mols, particularly 2 to 5 mols, of sulphur tetrafluoride are preferably reacted per mol of compound of the formula (II).

In process versions (b) and (d), inert organic solvents are suitable as diluents. The following solvents are used preferably: aliphatic, cyclic or aromatic, optionally halogenated hydrocarbons, such as, for example, benzine, benzene, toluene, xylene, pentane, hexane, heptane, cyclohexane, petroleum ether, ligroin, methylene chloride, chloroform, carbon tetrachloride, chlorobenzene or dichlorobenzene, ethers such as diethyl ether, diisopropyl ether, dioxane, tetrahydrofuran or ethylene glycol diethyl ether or dimethyl ether, ketones such as acetone, butanone, methyl isopropyl ketone or methyl isobutyl ketone, esters such as ethyl acetate, nitriles, such as acetonitrile or propionitrile, or amides such as dimethylformamide, dimethylacetamide, N-methylpyrrolidone or hexamethylphosphoric triamide. However, the process versions (b) and (d) can alternatively be carried out in alcohol or in an aqueous system, for example in two phases with addition of phase transfer catalysts.

However, it is also possible to employ the compounds of the formula (III), used as reactants, as diluents in appropriate excess.

All inorganic and organic bases which can conventionally be used are suitable as acid acceptors for carrying out the preparation processes (b) and (d). Alkali metal hydrides, hydroxides, amides, carbonates or bicarbonates, such as, for example, sodium hydride, sodium amide, sodium hydroxide, sodium carbonate or sodium bicarbonate, or alternatively tertiary amines, such as, for example, triethylamine, N,N-dimethylaniline, pyridine, 4-(N,N-dimethylamino)-pyridine, diazabicyclooctane (DABCO), diazobicyclononene (DBN) or diazabicycloundecene (DBU), are used preferably.

The reaction temperatures can be varied within a relatively wide range when carrying out the preparation processes (b) and (d). In general, the reactions are carried out at temperatures between −20° C. and +150° C.

In process version (c), inert organic or inorganic solvents are suitable as diluents, alcohols such as methanol or ethanol, or their mixtures with water, being particularly suitable.

The process (c) is carried out either in the presence of a strong acid, such as, for example, hydrochloric acid, trifluoroacetic acid or hydrobromic acid, in glacial acetic acid or in the presence of a base. Aqueous solutions of sodium hydroxide or potassium hydroxide are preferred as bases.

The reaction temperatures can be varied within a relatively wide range when carrying out the process (c) according to the invention. In general, the process is carried out at temperatures between −20° C. and +150° C., preferably at temperatures between 0° C. and +120° C.

To carry out the process (c), 1 to 30 mols, preferably 1 to 15 mols, of acid or base are, in general, employed per mol of 5-(N-acylamino)-4-trifluoromethyl-1-arylpyrazole of the formula (If). The reaction is carried out, and the reaction products of the formula (Ie) are worked up and isolated, in a generally conventional fashion.

The active compounds are suitable for combating animal pests, in particular insects, and arachnida, which are encountered in agriculture, in forestry, in the protection of stored products and of materials, and in the hygiene field and have good plant tolerance and favorable toxicity to warm-blooded animals. They are active against normally sensitive and resistant species and against all or some stages of development.

The abovementioned pests include:

From the order of the Isopoda, for example, *Oniscus asellus*, *Armadillidium vulgare* and *Porcellio scaber*. From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis*, *Periplaneta americana*, *Leucophaea maderae*, *Blattella germanica*, *Acheta domesticus*, Gryllotalpa spp., *Locusta migratoria migratorioides*, *Melanoplus differentialis* and *Schistocerca gregaria*. From the order of the Dermaptera, for example, *Forficula auricularia*. From the order of the Isoptera, for example, Reticulitermes spp.. From the order of the Anoplura, for example, *Phylloxera vastatrix*, Pemphigus spp., *Pediculus humanus corporis*, Haematopinus spp. and Linognathus spp. From the order of the Mallophaga, for example, Trichodectes spp. and Damalinea spp. From the order of the Thysanoptera, for example, *Hercinothrips femoralis* and Thrips tabaci. From the order of the Heteroptera, for example, Eurygaster spp., *Dysdercus intermedius*, *Piesma quadrata*, *Cimex lectularius*, *Rhodnius prolixus* and Triatoma spp. From the order of the Homoptera, for example, *Aleurodes brassicae*, *Bemisia tabaci*, *Trialeurodes vaporariorum*, *Aphis gossypii*, *Brevicoryne brassicae*, *Cryptomyzus ribis*, *Doralis fabae*, *Doralis pomi*, *Eriosoma Lanigerum*, *Hyalopterus arundinis*, *Macrosiphum avenae*, *Myzus* spp., *Phorodon humuli*, *Rhopalosiphum padi*, Empoasca spp., *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, Pseudococcus spp. and Psylla spp. From the order of the Lepidoptera, for example, *Pectinophora gossypiella*, *Bupalus piniarius*, *Cheimatobia brumata*, *Lithocolletis blancardella*, *Hyponomeuta padella*, *Plutella maculipennis*, *Malacosoma neustria*, *Euproctis chrysorrhoea*, Lymantria spp. *Bucculatrix thurberiella*, *Phyllocnistis citrella*, Agrotis spp., Euxoa spp., Feltia spp., *Earias insulana*, Heliothis spp., *Laphygma exigua*, *Mamestra brassicae*, *Panolis flammea*, *Prodenia litura*, Spodoptera spp., *Trichoplusia ni*, *Carpocapsa pomonella*, Pieris spp., Chilo spp., *Pyrausta nubilalis*, *Ephestia kuehniella*, *Galleria mellonella*, *Tineola bisselliella*, *Tinea pellionella*, *Hofmannophila pseudospretella*, *Cacoecia podana*, *Capua reticulana*, *Choristoneura fumiferana*, *Clysia ambiguella*, *Homona magnanima* and *Tortrix viridana*. From the order of the Coleoptera, for example, *Anobium punctatum*, *Rhizopertha dominica*, *Bruchidius obtectus*, *Acanthoscelides obtectus*, *Hylotrupes bajulus*, *Agelastica alni*, *Leptinotarsa decemlineata*, *Phaedon cochleariae*, Diabrotica spp., *Psylliodes chrysocephala*, *Epilachna varivestis*, Atomaria spp., *Oryzaephilus surinamensis*, Anthonomus spp., Sitophilus spp., *Otiorrhynchus sulcatus*, *Cosmopolites sordidus*, *Ceuthorrhynchus assimilis*, *Hypera postica*, Dermestes spp., Trogoderma spp., Anthrenus spp., Attagenus spp., Lyctus spp., *Meligethes aeneus*, Ptinus spp., *Niptus hololeucus*, *Gibbium psylloides*, Tribolium spp., *Tenebrio molitor*, Agriotes spp., Conoderus spp., *Melolontha melolontha*, *Amphimallon solstitialis* and *Costelytra zealandica*. From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus*, Oscinella frit, Phorbia spp., *Pegomyia hyoscyami*, *Ceratitis capitata*, *Dacus oleae* and *Tipula paludosa*. From the order of the Siphonaptera, for example, *Xenopsylla cheopis* and Ceratophyllus spp. From the order of the Arachnida, for example, *Scorpio maurus* and *Latrodectus mactans*. From the order of the Acarina, for example, *Acarus siro*, Argas spp., Ornithodoros spp., *Dermanyssus gallinae*, *Eriophyes ribis*, *Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The active compounds of the formula (I) which can be used according to the invention are distinguished by a strong insecticidal and acaricidal action. They can be employed, in particular, against insects which are harmful to plants, such as, for example, against the caterpillars of the cabbage moth (*Plutella maculipennis*) or against the larvae of the mustard beetle (*Phaedon cochleariae*), and against mites which are harmful to plants, such as, for example, against the two-spotted spider mite (*Tetranychus urticae*). In addition, they are extremely suitable for combating soil insects and can be employed, for example, for combating *Phorbia antiqua* grubs, *Myzus persicae* and *Diabrotica balteata*. A notable root-systemic action, for example against *Phaedon cochleariae* larvae, should be emphasized.

In addition, the active compounds of the formula (I) which can be used according to the invention have a strong action against hygiene pests and stored product pests and can be employed, for example, for combating the oriental cockroach (*Blatta orientalis*), german cockroach (*Blattella germanica*) or for combating the granary weevil (*Sitophilus granarius*). Furthermore, the active compounds according to the invention can be employed particularly successfully for combating pests which live parasitically on warm-blooded animals both ecto- and endoparaistes, such as, for example, against the larvae of the greenbottle fly (*Lucilia cuprina*), against cattle ticks (*Boophilus microplus*), against predacious mites (*Psoroptes ovis*), against biting flies (*Stomoxys calcitrans*) or against the face fly (*Musca autumnalis*).

In addition, the active compounds of the formula (I) which can be used according to the invention also have a good plant growth regulation.

When applied in appropriate amounts, the active compounds of the formula (I) which can be used according to the invention additionally display a herbicidal action.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds which can be used according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds which can be used according to the invention can furthermore be present in their commercially available formulations and in the use forms, prepared from from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds which can be used according to the invention are also suitable for combating insects, midges, ticks etc. in the sectors of animal keeping and cattle breeding; better results, for example higher milk production, greater weight, more attractive animal pelt, longer life etc., can be achieved by combating the pests.

The application of the active compounds which can be used according to the invention occurs in these sectors in a known fashion, such as by means of external application in the form of, for example, dipping, spraying, pouring-on, spotting-on and dusting.

The preparation and use of the active compounds is evident from the examples below.

PREPARATION EXAMPLES

EXAMPLE 1

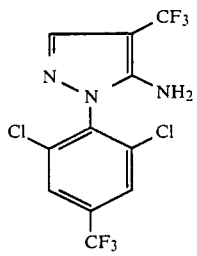

30.8 g (0.1 mol) of 5-amino-1-(2,6-dichloro-4-trifluoromethylphenyl)-4-carboxypyrazole, 100 ml of anhydrous hydrofluoric acid and 40 g of sulphur tetrafluoride are stirred for 8 hours at 120° C. in a steel autoclave under a nitrogen atmosphere. The pressure is subsequently released at room temperature, hydrofluoric acid which still remains is removed by distillation, and the residue is poured onto 500 ml of ice water. This mixture is made alkaline by dropwise addition of concentrated sodium hydroxide solution. The solid which is produced is filtered off under suction and washed with diethyl ether. The filtrate is extracted twice with diethyl ether. After drying over anhydrous magnesium sulphate, the solvent is removed and the solid residue which remains is filtered chromatographically through a short silica gel column (eluent: methylene chloride). The pure product remains after removal of the solvent. 26.6 g (73% of theory) of 5-amino-1-(2,6-dichloro-4-trifluoromethyl-phenyl)-4-trifluoromethylpyrazole of melting point 106° C. are obtained.

The examples listed in the table below are produced by the same process, a mixture of methylene chloride/petroleum ether 4:1 being employed as an eluent in the short silica gel column in Examples 2 and 3, and pure methylene chloride being employed as an eluent in the other examples.

General formula:

| Ex. | R¹ | R² | R³ | R⁴ | Ar | M.p. [°C.] |
|---|---|---|---|---|---|---|
| 2 | H | CF₃ | H | H | 2,4,6-trichlorophenyl | 98–99 |
| 3 | H | CF₃ | H | H | 2,6-dibromo-4-trifluoromethylphenyl | 148–150 |
| 4 | CH₃ | CF₃ | H | H | 2,6-dichloro-4-trifluoromethylphenyl | 131–133 |
| 5 | C₂H₅ | CF₃ | H | H | 2,4,6-trichlorophenyl | 107–109 |
| 6 | H | CF₃ | H | H | 4-bromo-2,6-dichlorophenyl | 98 |
| 7 | H | CF₃ | H | H | 3-chloro-4-trifluoromethylphenyl | 96–97 |
| 8 | H | CF₃ | H | H | 2,6-dichloro-4-trifluoromethoxyphenyl | |
| 9 | H | CF₃ | H | H | 2-chloro-6-bromo-4-trifluoromethylphenyl | |
| 10 | H | CF₃ | CH₃ | H | 2-chloro-4-trifluoromethoxyphenyl | |
| 11 | H | CF₃ | CH₃ | CH₃ | 3,5-dichloropyridyl | |
| 12 | CH₃ | CF₃ | H | H | 2-chloro-4-trifluoromethylphenyl | |
| 13 | CH₃ | CF₃ | C₂H₅ | H | 2,6-dichloro-4-trifluoromethoxyphenyl | |
| 14 | CH₃ | CF₃ | C₂H₅ | C₂H₅ | 3,5-dichloropyridyl | |

EXAMPLE 15

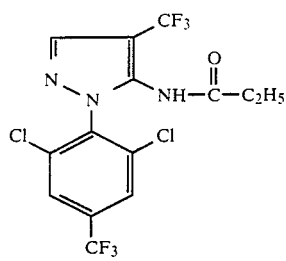

A mixture comprising 11 g (0.03 mol) of 5-amino-1-(2,6-dichloro-4-trifluoromethyl-phenyl)-4-trifluoromethyl-pyrazole, 5 g of propionic anhydride and 0.5 ml of concentrated sulphuric acid is stirred for 8 hours at 60° C. in 50 ml of acetonitrile. After cooling, the preparation is poured into water and extracted with methylene chloride, and the organic phase is dried over sodium sulphate and subsequently concentrated in vacuo. The residue is recrystallized from ligroin. Yield: 9.3 g of 5-propionylamino-1-(2,6-dichloro-4-trifluoromethyl-phenyl)-4-trifluoromethyl-pyrazole of melting point 136°–140° C.

The compounds of the following Examples 16–23 are prepared by an analogous route.

General formula:

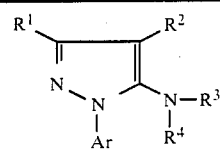

| Ex. | R$^1$ | R$^2$ | R$^3$ | R$^4$ | Ar | M.p. [°C.] |
|---|---|---|---|---|---|---|
| 16 | H | CF$_3$ | H | COC$_2$H$_5$ | ![Cl,CF3,Cl phenyl] | 136–140 |
| 17 | H | CF$_3$ | H | COCH$_3$ | " | 126–130 |
| 18 | H | CF$_3$ | H | COCF$_3$ | " | 130 |
| 19 | H | CF$_3$ | H | COCHCl$_2$ | " | 135–138 |
| 20 | H | CF$_3$ | H | COCH$_2$Cl | " | 128–130 |
| 21 | H | CF$_3$ | H | COC$_2$H$_5$ | ![Cl,Cl pyridine] | |
| 22 | H | CF$_3$ | H | COCH$_3$ | " | |
| 23 | H | CF$_3$ | H | COCF$_3$ | " | |
| 24 | H | CF$_3$ | CH$_3$ | COCH$_3$ | ![Cl,CF3,Cl phenyl] | 120–124 |

-continued

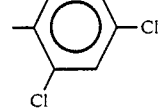

| Ex. | R$^1$ | R$^2$ | R$^3$ | R$^4$ | Ar | M.p. [°C.] |
|---|---|---|---|---|---|---|
| 25 | H | CF$_3$ | H | COC$_2$H$_5$ | ![Cl,Cl,Cl phenyl] | 133 |

Preparation of starting compounds:

EXAMPLE (A)

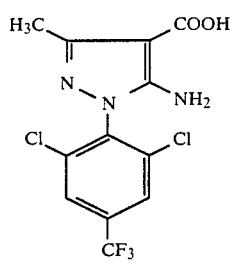

35.4 g (0.1 mol) of 5-amino-1-(2,6-dichloro-4-trifluoromethyl-phenyl)-4-carbethoxy-pyrazole are heated under reflux for 24 hours in a solution of 8 g (0.2 mol) of sodium hydroxide, 24 ml of water and 100 ml of ethanol. 450 ml of water are subsequently added, and the mixture is washed twice with 70 ml of diethyl ether. The alcohol is removed from the aqueous phase by distillation, and 20 ml of concentrated hydrochloric acid are then added with ice cooling. The suspension is cooled to 5° C., and the precipitate is filtered off under suction, washed with water until neutral, and dried. 26.2 g (74% of theory) of the compound 5-amino-1-(2,6-dichloro-4-trifluoromethylphenyl)-4-carboxy-pyrazole of melting point 158° C. (decomposition) are obtained.

The following are prepared in a corresponding fashion:

General formula:

| R$^1$ | Ar | M.p. [°C.] |
|---|---|---|
| H | ![Cl,Cl phenyl] | 186 |

-continued

General formula:

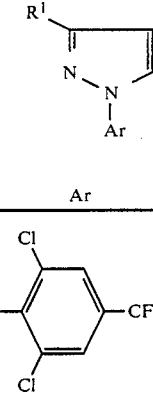

| R¹ | Ar | M.p. [°C.] |
|---|---|---|
| H | 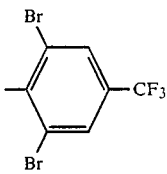 2,6-Cl₂-4-CF₃-phenyl | 188–190 (decomp.) |
| H | 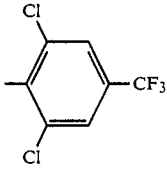 2,6-Br₂-4-CF₃-phenyl | 220 |
| CH₃ | 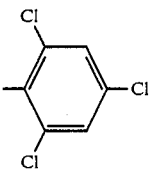 2,6-Cl₂-4-CF₃-phenyl | 158 (decomp.) |
| C₂H₅ | 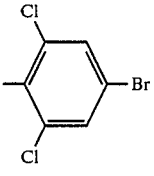 2,4,6-trichlorophenyl | 158 (decomp.) |
| H | 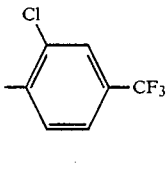 2,6-Cl₂-4-Br-phenyl | 163 |
| H | 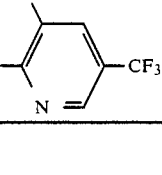 2-Cl-4-CF₃-phenyl | 180 (decomp.) |
| H | 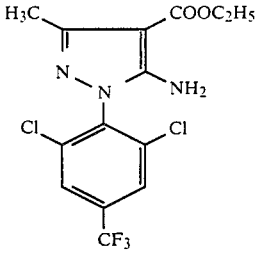 3-Cl-5-CF₃-pyridyl | |

EXAMPLE (B)

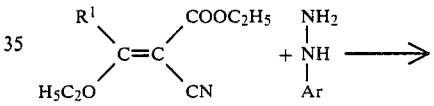

245 g (1 mol) of 2,6-dichloro-4-trifluoromethyl-phenylhydrazine and 183 g (1 mol) of methyl-ethoxymethylenemalonic acid monoethyl ester nitrile are dissolved in 2.5 l of ethanol and stirred for 10 hours at the reflux temperature. The solvent is subsequently removed in a rotary evaporator and the residue is taken up in methylene chloride. The residue is then washed with water, dried in diethyl ether over magnesium sulphate, filtered and concentrated. The residue is distilled incipiently in a high vacuum at 90° C. 290 g (75% of theory) of 5-amino-1-(2,6-dichloro-4-trifluoromethylphenyl)-3-methyl-4-carbethoxy-pyrazole of melting point 104°–108° C. remain.

The following are prepared in a corresponding fashion according to the following equation:

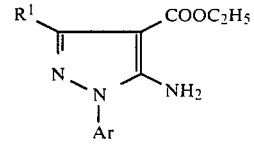

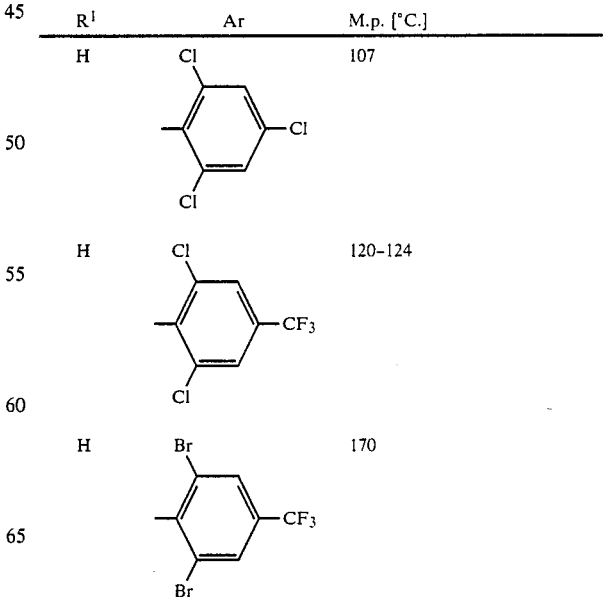

| R¹ | Ar | M.p. [°C.] |
|---|---|---|
| H | 2,4,6-trichlorophenyl | 107 |
| H | 2,6-Cl₂-4-CF₃-phenyl | 120–124 |
| H | 2,6-Br₂-4-CF₃-phenyl | 170 |

-continued

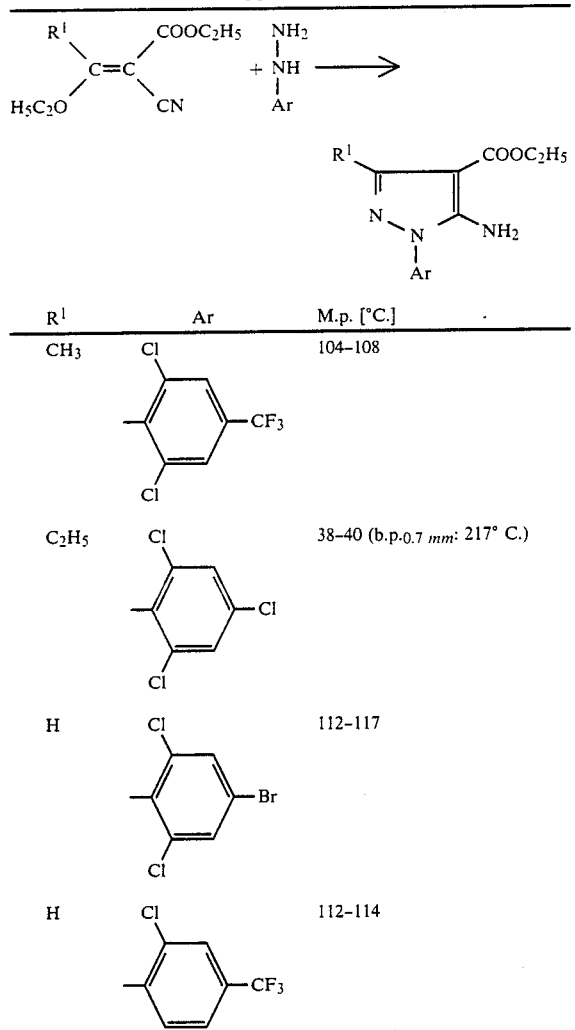

| $R^1$ | Ar | M.p. [°C.] |
|---|---|---|
| $CH_3$ | 2,4-Cl, 4-CF₃ phenyl (dichloro-trifluoromethylphenyl) | 104–108 |
| $C_2H_5$ | 2,4,5-trichlorophenyl | 38–40 (b.p.$_{0.7\,mm}$: 217° C.) |
| H | 2,4-dichloro-5-bromophenyl | 112–117 |
| H | 3-chloro-5-trifluoromethylphenyl | 112–114 |

EXAMPLE A

Phaedon larvae test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After the specified period of time, the destruction in % is determined. 100% means that all the beetle larvae have been killed; 0% means that none of the beetle larvae have been killed.

In this test, the following compounds of the preparation examples, for example, display superior activity compared to the prior art: 1, 4, 7, 15 and 17.

EXAMPLE B

Plutella test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*), as long as the leaves are still moist.

After the specified periods of time, the destruction in % is determined. 100% means that all the caterpillars have been killed; 0% means that none of the caterpillars have been killed.

In this test, the following compounds of the preparation examples, for example, display superior activity compared to the prior art: 1, 4, 15 and 17.

EXAMPLE C

Test insect: *Phorbia antiqua* maggots (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The soil is filled into pots and the pots are left to stand at room temperature.

After 24 hours, the test animals are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, the following compounds of the preparation examples, for example, display superior activity compared to the prior art: 3, 4 and 15.

EXAMPLE D

Test insect: *Diabrotica bateata* larvae (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration. The preparation of active compound is intimately mixed with soil. The concentration of the active compound in the preparation is of practically no importance here, only the amount by weight of active compound per unit volume of soil, which is given in ppm (=mg/l), being decisive. The soil is filled into 0.5 l pots and the pots are left to stand at 20° C.

Immediately after preparation, 6 pre-germinated corn seeds are placed in each pot. After 2 days, the appropriate test animals are introduced into the treated soil. After a further 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, the following compounds of the preparation examples, for example, display superior activity compared to the prior art: 4 and 15.

EXAMPLE E

Root-systemic action
Test insect: *Phaedon cochleariae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifer is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is filled into pots and these are planted with cabbage (*Brassica oleracea*). The active compound can in this way be taken up from the soil by the roots of the plants and be transported into the leaves.

To demonstrate the root-systemic effect, exclusively the leaves are infested with the abovementioned test insects after 7 days. After a further 2 days, the evaluation is made by counting or estimating the dead insects The root-systemic action of the active compound is deduced from the mortality figures. It is 100% if all test insects have been killed and 0% if just as many test insects are still alive as in the case of the untreated control.

In this test, the following compound of the preparation examples, for example, displays superior activity compared to the prior art: 15.

EXAMPLE F

Root-systemic action
Test insect: *Myzus persicae*
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is filled into pots and these are planted with cabbage (*Brassica oleracea*). The active compound can in this way be taken up from the soil by the roots of the plants and transported into the leaves.

To demonstrate the root-systemic effect, exclusively the leaves are infested with the abovementioned test insects after 7 days. After a further 2 days, the evaluation is made by counting or estimating the dead insects The root-systemic action of the active compound is deduced from the mortality figures. It is 100% if all test insects have been killed and 0% if just as many test insects are still alive as in the case of the untreated control.

In this test, the following compounds of the preparation examples, for example, display superior activity compared to the prior art: 15 and 17.

EXAMPLE G

Test insects: *Sitophilus granarius*
Number of test insects: 25
Solvent: Acetone 2 parts by weight of active compound are taken up in 1,000 parts by volume of solvent. The solution thus obtained is diluted with further solvent to the desired concentration.

2.5 ml of the active compound solution are pipetted into a Petri dish. A filter paper disc of about 9.5 cm diameter is located on the bottom of the Petri dish. The Petri dish is left standing open until the solvent has completely evaporated. The amount of active compound per $m^2$ of filter paper varies, depending on the concentration of the active compound solution. The stated number of test insects is then introduced into the Petri dish, and the dish is covered with a glass lid.

The condition of the test insects is checked 3 days after the experiments have been set up. The destruction in % is determined. 100% means that all the test insects have been killed; 0% means that none of the test insects have been killed.

In this test, the following compounds of the preparation examples, for example, display superior activity compared to the prior art: 1, 4, 6, 15, 17, 18 and 19.

EXAMPLE H

Test insects: *Blatella germanica*
Number of test insects: 20
Solvent: Acetone 2 parts by weight of active compound are taken up in 1,000 parts by volume of solvent. The solution thus obtained is diluted with further solvent to the desired concentration.

2.5 ml of the active compound solution are pipetted into a Petri dish. A filter paper disc of about 9.5 cm diameter is located on the bottom of the Petri dish. The Petri dish is left standing open until the solvent has completely evaporated. The amount of active compound per $m^2$ of filter paper varies, depending on the concentration of the active compound solution. The stated number of test insects is then introduced into the Petri dish, and the dish is covered with a glass lid.

The condition of the test insects is checked 3 days after the experiments have been set up. The destruction in % is determined. 100% means that all the test insects have been killed; 0% means that none of the test insects have been killed.

In this test, the following compounds of the preparation examples, for example, display superior activity compared to the prior art: 1, 4, 15, 18 and 19.

EXAMPLE J

Test insects: *Musca domestica*
Number of test insects: 25
Solvent: Acetone 2 parts by weight of active compound are taken up in 1,000 parts by volume of solvent. The solution thus obtained is diluted with further solvent to the desired lower concentrations.

2.5 ml of the active compound solution are pipetted into a Petri dish. A filter paper of about 9.5 cm diameter is located on the bottom of the Petri dish. The Petri dish is left standing open until the solvent has completely evaporated. The amount of active compound per m$^2$ of filter paper varies, depending on the concentration of the active compound solution. The stated number of test insects is then introduced into the Petri dish, and the dish is covered with a glass lid.

The condition of the test insects is checked continuously. The time required for a 100% knock-down effect is determined.

In this test, the following compounds of the preparation examples, for example, display superior activity compared to the prior art: 1, 4, 17 and 19.

EXAMPLE K

Test with *Boophilus microplus* resistant/OP-resistant Biarra strain
Solvent:
  35 parts by weight of ethylene glycol monomethyl ether
  35 parts by weight of nonylphenol polyglycol ether To produce a suitable preparation of active compound, three parts by weight of active compound are mixed with seven parts by weight of the solvent mixture indicated above, and the concentrate thus obtained is diluted with water to the desired concentration.

10 adult *Boophilus microplus* res. are immersed for 1 minute in the active compound preparation to be tested. After transfer to plastic beakers and storage in a climatically controlled chamber, the degree of destruction is determined.

In this test, for example, the following compound from the preparation examples shows a superior activity compared to the prior art: 1

EXAMPLE L

Test with *Lucilia cuprina* larvae (OP-resistant Goondiwindi strain)
Emulsifier:
  35 parts by weight of ethylene glycol monomethyl ether
  35 parts by weight of nonylphenol polyglycol ether To produce a suitable preparation of active compound, three parts by weight of active compound are mixed with seven parts by weight of the abovementioned emulsifier mixture and the concentrate thus obtained is diluted with water to the particular desired concentration.

About 20 *Lucilia cuprina* res. larvae are introduced into a test tube which contains approx. 1 cm$^2$ of horse flesh and 0.5 ml of the preparation of active compound. After 24 hours, the degree of destruction is determined.

In this test, the following compound of the preparation examples, for example, activity compared to the prior art: 1 and 3.

EXAMPLE M

Test with *Stomoxys calcitrans*
Emulsifier:
  35 parts by weight of ethylene glycol monomethyl ether
  35 parts by weight of nonylphenol polyglycol ether To produce a suitable preparation of active compound, three parts by weight of active compound are mixed with seven parts by weight of the emulsifier mixture indicated above, and the concentrate thus obtained is diluted with water to the particular desired concentration.

10 adult *Stomoxys calcitrans* are placed in Petri dishes containing filter paper discs of appropriate size which had been saturated one day before the start of the experiment with 1 ml of the active compound preparation to be tested. After 3 hours, the degree of destruction is determined.

In this test, the following compound of the preparation examples, for example, displays superior activity compared to the prior art: 1

EXAMPLE N

Facefly test (*Musca autumnalis*)
Solvent:
  35 parts by weight of ethylene glycol monomethyl ether
  35 parts by weight of nonylphenol polyglycol ether To produce a suitable formulation, three parts by weight of active compound are diluted with seven parts of the abovementioned solvent/emulsifier mixture and the emulsion concentrate thus obtained is diluted with water to the particular desired concentration.

10 adult faceflies (*Musca autumnalis*) are introduced into Petri dishes containing filter paper discs of appropriate size which have been impregnated one day before the start of the test with 1 ml of the active compound preparation to be tested. After 3 hours, the degree of destruction is determined in percent, 100% meaning that all of the flies have been destroyed and 0% meaning that no flies have been destroyed.

In this test, for example, the following compound from the preparation examples shows a superior action compared with the prior art: 1.

EXAMPLE O

Test with *Psoroptes ovis*
Solvent:
  35 parts by weight of ethylene glycol monomethyl ether
  35 parts by weight of nonylphenol polyglycol ether To produce a suitable preparation of active compound, three parts by weight of active compound are mixed with seven parts by weight of the solvent mixture indicated above, and the concentrate thus obtained is diluted with water to the desired concentration.

About 10–25 *Psoroptes ovis* are introduced into 1 ml of the active compound preparation to be tested, which has been pipetted into tablet nests of a deepdrawing pack. After 24 hours, the degree of destruction is determined.

In this test, the following compound of the preparation examples, for example, displays superior activity compared to the prior art: 3

It is understood that the specification and examples are illustrative but not limitative of the present invention and that other embodiments within the spirit and scope of the invention will suggest themselves to those skilled in the art.

We claim:

1. A method of combating insects and acarids which comprises applying to such insects, acarids or a habitat thereof, an insecticidally or acaricidally effective amount of a 5-amino-1-aryl-pyrazole of the formula

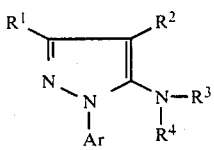

in which
- $R^1$ represents in each case straight-chain or branched alkyl or halogenoalkyl having 1 to 4 carbon atoms and, if appropriate, 1 to 9 identical or different halogen atoms, or hydrogen,
- $R^2$ represents trifluoromethyl,
- $R^3$ represents hydrogen, $C_1$–$C_6$-alkyl or $C_2$–$C_6$-alkenyl,
- $R^4$ represents hydrogen, $C_1$–$C_6$-alkyl, $C_2$–$C_6$-alkenyl, $C_2$–$C_6$-alkinyl or a

radical, where $R^5$ represents $C_1$–$C_4$-alkyl or $C_1$–$C_4$-halogenoalkyl,
Ar represents in each case optionally mono- or polysubstituted phenyl, 2-pyridyl, 3-pyridyl or 4-pyridyl, the substituents being identical or different and being cyano, nitro, halogen, in each case straight-chain or branched alkyl, alkoxy or alkoxycarbonyl each having up to 4 carbon atoms, in addition in each case straight-chain or branched halogenoalkyl or halogenoalkoxy each having up to 4 carbon atoms and up to 9 identical or different halogen atoms, or an —S(O)$_m$—R$^6$ radical where
$R^6$ represents amino, and in each case straight-chain or branched alkyl, alkylamino, dialkylamino lor halogenoalkyl each having up to 4 carbon atoms in the individual alkyl parts and, in the case of halogenoalkyl, having up to 9 identical or different halogen atoms, and
m represents the number 0, 1 or 2.

2. The method according to claim 1 in which
- $R^1$ represents hydrogen, methyl, ethyl, n- or i-propyl or trifluoromethyl,
- $R^2$ represents trifluoromethyl,
- $R^3$ represents hydrogen, methyl, ethyl, n- or i-propyl, n-, i-, s- or t-butyl, n- or i-pentyl, n- or i-hexyl, vinyl, prop-1-enyl, prop-2-enyl, but-1-enyl or but-2-enyl,
- $R^4$ represents hydrogen, methyl, ethyl, n- or i-propyl, n-, i-, s- or t-butyl, n- or i-pentyl, n- or i-hexyl, propargyl, but-1-inyl, but-2-inyl or one of the radicals

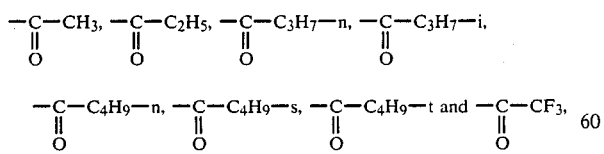

Ar represents in each case optionally mono- to pentasubstituted phenyl, 2-pyridyl, 3-pyridyl or 4-pyridyl, the substituents being identical or different and being cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, difluorochloromethyl, dichlorofluoromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or an —S(O)$_m$—R$^6$ radical, where
$R^6$ represents amino, methylamino, ethylamino dimethylamino, diethylamino, fluorodichloromethyl, difluoromethyl, tetrafluoroethyl, trifluorochloroethyl, trifluoromethyl, methyl or ethyl, and
m represents a number 0, 1 or 2.

3. The method according to claim 1, in which
- $R^1$ represents hydrogen, alkyl or halogenoalkyl,
- $R^2$ represents trifluoromethyl,
- $R^3$ represents hydrogen, alkyl or alkenyl,
- $R^4$ represents hydrogen, alkyl, alkenyl, alkinyl or a

radical,
Ar represents in each case optionally substituted phenyl or pyridyl,
where
X represents oxygen or sulphur, and
$R^5$ represents alkyl or halogenoalkyl, where, if $R^1$ represents hydrogen, the radicals $R^3$, $R^4$ and Ar may not have the following combinations of meanings:

$R^3$=hydrogen, $R^4$=hydrogen and Ar=2,4,6-trichlorophenyl or 2,4,6-trinitrophenyl;

$R^3$=hydrogen, $R^4$=COCH$_3$ and Ar=2,6,dichloro-4-trifluoromethylphenyl or 2,6-dichloro-4-trifluoromethyloxyphenyl;

$R^3$=hydrogen, $R^4$=COC$_2$H$_5$ and Ar=2,6-dichloro-4-trifluoromethylthiophenyl or 2,3,6-trifluoro-4-trifluoromethylthiophenyl;

$R^3$=methyl, $R^4$=COCH$_3$ and Ar=2-chloro-4-trifluoromethyl.

4. The method according to claim 1, wherein such compound is 5-amino-1-(2,6-dichloro-4-trifluoromethylphenyl)-3-methyl-4-trifluoromethylpyrazole of the formula

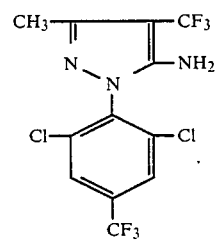

* * * * *